US00PP36052P2

(12) United States Plant Patent
van der Meer

(10) Patent No.: US PP36,052 P2
(45) Date of Patent: Jul. 30, 2024

(54) ***ASTILBE* PLANT NAMED 'GO GO RED'**

(50) Latin Name: ***Astilbe chinensis* X *Astilbe arendsii***
Varietal Denomination: Go Go Red

(71) Applicant: Hans van der Meer, Nieuwe Wetering (NL)

(72) Inventor: Hans van der Meer, Nieuwe Wetering (NL)

( * ) Notice: Subject to any disclaimer, the term of this patent is extended or adjusted under 35 U.S.C. 154(b) by 0 days.

(21) Appl. No.: 18/133,513

(22) Filed: Apr. 11, 2023

(51) Int. Cl.
*A01H 5/02* (2018.01)
*A01H 6/80* (2018.01)

(52) U.S. Cl.
USPC ..... Plt./407
CPC ..... *A01H 6/80* (2018.05)

(58) Field of Classification Search
USPC ..... Plt./407
CPC ..... A01H 5/02
See application file for complete search history.

(56) References Cited

PUBLICATIONS

CPVO Application Consultation, version 4.10.8, Citation for *Astilbe* 'Go Go Red'; Aug. 9, 2023.*

* cited by examiner

*Primary Examiner* — Kent L Bell
(74) *Attorney, Agent, or Firm* — C. Anne Whealy

(57) ABSTRACT

A new and distinct cultivar of *Astilbe* plant named 'Go Go Red', characterized by its relatively compact and broadly upright plant habit; vigorous growth habit; dark green-colored leaves; freely and uniformly flowering habit; long flowering period; reddish purple-colored flowers on upright and strong peduncles; and good container and garden performance.

2 Drawing Sheets

Figure 1:
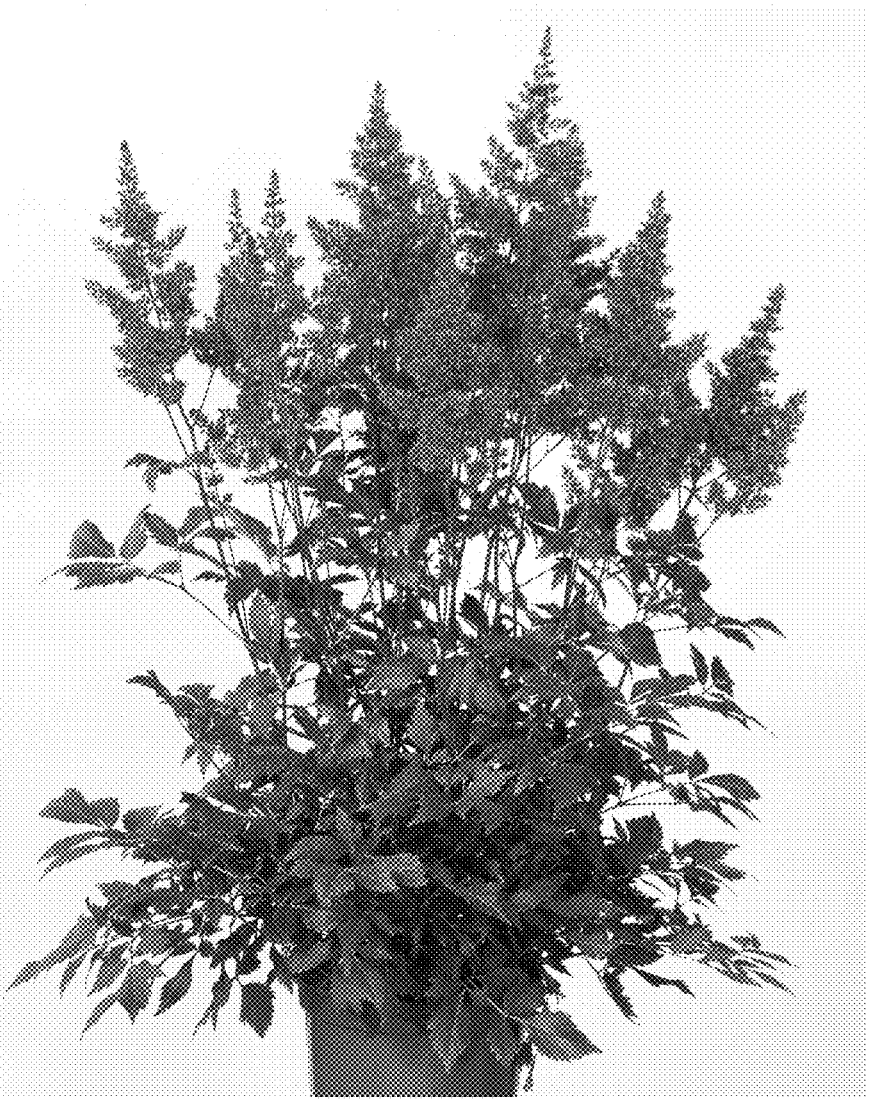

Botanical designation: *Astilbe chinensis* X *Astilbe arendsii.*

Cultivar denomination: 'GO GO RED'.

BACKGROUND OF THE INVENTION

The present invention relates to a new and distinct cultivar of *Astilbe* plant, botanically known as *Astilbe chinensis* X *Astilbe arendsii* and hereinafter referred to by the name 'Go Go Red'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2013 in Nieuwe Wetering, The Netherlands, of *Astilbe chinensis* 'Harvandermeer', not patented, as the female, or seed, parent with an unknown seedling selection of *Astilbe arendsii* as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2015.

Asexual reproduction of the new *Astilbe* plant by vegetative divisions in a controlled nursery environment in Nieuwe Wetering, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Go Go Red'. These characteristics in combination distinguish 'Go Go Red' as a new and distinct *Astilbe* plant:

1. Relatively compact and broadly upright plant habit.
2. Vigorous growth habit.
3. Dark green-colored leaves.
4. Freely and uniformly flowering habit.
5. Long flowering period.
6. Reddish purple-colored flowers on upright and strong peduncles.
7. Good container and garden performance.

Plants of the new *Astilbe* differ primarily from plants of the female parent, 'Harvandermeer', in the following characteristics:

1. Plants of the new *Astilbe* are more compact than plants of 'Harvandermeer'.
2. Plants of the new *Astilbe* flower for a longer period of time than plants of 'Harvandermeer'.

Plants of the new *Astilbe* can be compared to plants of *Astilbe japonica* 'Red Sentinel', not patented. In side-by-side comparisons, plants of the new *Astilbe* and 'Red Sentinel' differ primarily in the following characteristics:

1. Plants of the new *Astilbe* are more compact than plants of 'Red Sentinel'.
2. Plants of the new *Astilbe* have smaller flowers than plants of 'Red Sentinel'.
3. Plants of the new *Astilbe* flower for a longer period of time than plants of 'Red Sentinel'.

4. Flowers of plants of the new *Astilbe* are lighter and brighter reddish purple in color than flowers of plants of 'Red Sentinel'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1) is a side perspective view of a typical flowering plant of 'Go Go Red' grown in a container.

Figure 2:
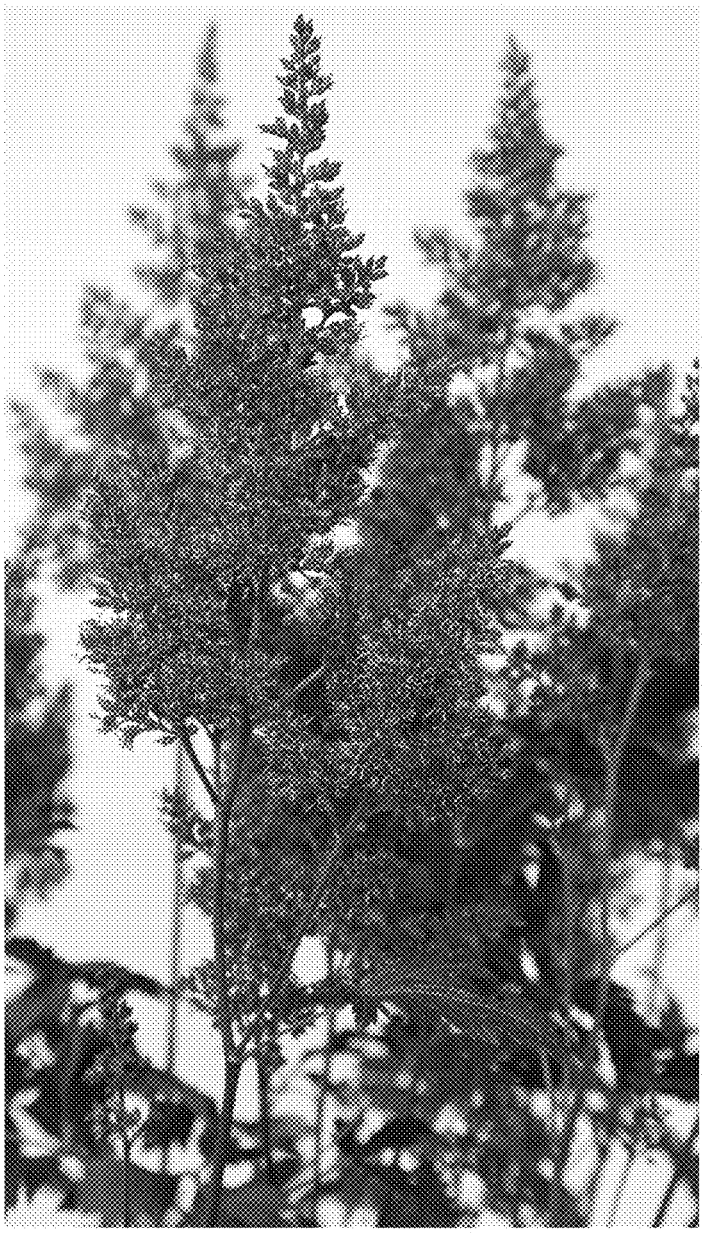

The photograph on the second sheet (FIG. 2) is a close-up view of typical inflorescences of 'Go Go Red'.

DETAILED BOTANICAL DESCRIPTION

The aforementioned photographs and following observations, measurements and values describe plants grown during the late summer in 15-cm containers in an outdoor nursery in Nieuwe Wetering, The Netherlands and under cultural practices typical of commercial *Astilbe* production. During the production of the plants, day temperatures ranged from 18C to 34C and night temperatures ranged from 10C to 20C. Plants were one year old when the photographs and description were taken. In the following description, color references are made to The Royal Horticultural Society Colour Chart, 2015 Edition, except where general tetms of ordinary dictionary significance are used.

Botanical classification: *Astilbe chinensis* X *Astilbe arendsii* 'Go Go Red'.

Parentage:

*Female, or seed, parent.*—*Astilbe chinensis* 'Harvandermeer', not patented.

*Male, or pollen, parent.*—Unknown seedling selection of *Astilbe arendsii*, not patented.

Propagation:

*Type.*—By vegetative divisions.

*Time to initiate roots.*—About three weeks at temperatures about 20C.

*Root description.*—Thick, fleshy; typically brown in color, actual color of the roots is dependent on substrate composition, water quality, fertilizer type and formulation.

*Rooting habit.*—Freely branching; dense.

Plant description:

*Plant form and growth habit.*—Herbaceous perennial; relatively compact and broadly upright plant habit with inflorescences held above the foliar plane on strong peduncles; flowering stems and leaves basal; freely flowering with numerous basal branches developing per plant, dense and bushy appearance; vigorous growth habit; and freely and uniformly flowering habit.

*Growth rate.*—Moderately rapid; from divisions, about three months are required to produce fully-grown flowering plants in containers.

*Plant height* (*soil level to top of foliar plane*).—About 33.4 cm.

*Plant height* (*soil level to top of inflorescences*).—About 55.6 cm.

*Plant width* (*spread*).—About 50.1 cm.

*Stem description.*—Quantity per plant: About 22 basal branches per plant. Length: About 25.2 cm. Diameter: About 3 mm. Internode length: About 12.6 cm. Strength: Strong. Aspect: Erect to about 15 degrees from vertical. Texture and luster: Sparsely pubescent; pubescence minute; glossy. Color, developing: Close to 152A. Color, at the internodes: Close to 145A strongly tinged with close to 182A and 182B. Color, developed: Close to 152A strongly tinged with close to a blend of N199B and N199C.

Leaf description:

*Arrangement.*—Alternate; biternately compound; on average, about 21 leaflets per leaf.

*Leaf length* (*excluding petiole*).—About 15.7 cm.

*Leaf width.*—About 19.6 cm.

*Terminal leaflet length.*—About 5.5 cm.

*Terminal leaflet width.*—About 2.4 cm.

*Lateral leaflet length.*—About 3.9 cm.

*Lateral leaflet width.*—About 1.8 cm.

*Leaf shape, in outline.*—Broadly ovate to broadly rhomboidal.

*Leaflet shape.*—Elliptic to narrowly elliptic to narrowly ovate.

*Leaflet apex.*—Narrowly acute.

*Leaflet base.*—Attenuate to narrowly cuneate.

*Leaflet margin.*—Biserrate.

*Leaflet texture and luster, upper surface.*—Moderately pubescent on the midvein and lateral venation; slightly glossy.

*Leaflet texture and luster, lower surface.*—Moderately pubescent on the midvein and lateral venation; moderately glossy.

*Leaflet venation pattern.*—Pinnate.

*Leaflet color.*—Developing leaflets, upper surface: Close to NN137B. Developing leaflets, lower surface: Close to a blend of 146A and 147B. Fully expanded leaflets, upper surface: Close to NN137B; venation, close to 144A. Fully expanded leaflets, lower surface: Close to a blend of 146A and147B; venation, close to 152D.

*Leaf petiole length.*—About 15 cm.

*Leaf petiole diameter.*—About 2 mm.

*Leaf and leaflet petiole strength.*—Strong.

*Leaf and leaflet petiole texture and luster, upper and lower surfaces.*—Sparsely pubescent; moderately glossy.

*Leaf and leaflet petiole color, upper surface.*—Close to 152D tinged with close to N199C.

*Leaf and leaflet petiole color, lower surface.*—Close to 144A tinged with close to 200D.

Flower description:

*Flower type and flowering habit.*—Single rotate flowers arranged on terminal compound panicles; flowers face upright, outward or downward depending on position on the inflorescence; panicles conical in shape; freely and uniformly flowering habit with about 2,700 flowers developing per inflorescence and about 60,000 flowers developing per plant during the flowering season.

*Fragrance.*—Moderately strong; sweet and pleasant.

*Natural flowering season.*—Plants begin flowering about 100 days after planting; continuously flowering from late spring until late summer in The Netherlands.

*Postproduction longevity.*—Flowers last about ten days on the plant; flowers not persistent.

*Flower buds.*—Height: About 2.75 mm. Diameter: About 1.5 mm. Shape: Broadly elliptic. Texture and luster: Smooth, glabrous; matte. Color: Sepals, close to 60D and petals, close to 64B.

*Inflorescence height.*—About 21.7 cm.

*Inflorescence diameter.*—About 10.5 cm.

*Flower diameter.*—About 6 mm by 6 mm.

*Flower depth.*—About 5 mm.

*Petals.*—Quantity per flower: Typically five in a single whorl. Length: About 4 mm. Width: About 0.75 mm. Shape: Oblanceolate. Apex: Obtuse. Base: Narrowly cuneate. Margin: Entire; occasionally with a single tooth on either side; not undulate. Texture and luster, upper and lower surfaces: Smooth, glabrous; matte. Color: Developing petals, upper surface: Close to 64C; distally, close to 64B. Developing petals, lower surface: Close to 64C. Fully expanded petals, upper and lower surfaces: Close to 70B; color becoming closer to N74C with subsequent development.

*Sepals.*—Quantity per flower: Typically five in a single whorl; towards the base forming a campanulate-shaped calyx. Calyx length: About 1.5 mm. Calyx diameter: About 2.5 mm. Length: About 1.5 mm. Width: About 0.7 mm. Shape: Ovate. Apex: Bluntly acute. Base: Cuneate, fused. Margin: Entire. Texture and luster, upper and lower surfaces: Smooth, glabrous; matte. Color: Developing sepals, upper surface: Close to 63B. Developing sepals, lower surface: Close to 63C; margin edges, close to 63B. Fully expanded sepals, upper and lower surfaces: Close to 60D; color does not change with subsequent development.

*Peduncles.*—Length: About 21.2 cm. Diameter: About 1.75 mm. Angle: Mostly erect. Strength: Strong. Texture and luster: Moderately to densely pubescent; moderately glossy. Color: Close to 152B.

*Pedicels.*—Length: About 2 mm. Diameter: About 0.5 mm. Angle: About 40 degrees from peduncle axis. Strength: Moderately strong. Texture and luster: Moderately pubescent; matte. Color: Close to 59D.

*Reproductive organs.*—Stamens: Quantity per flower: Typically ten. Filament length: About 2 mm. Filament color: Close to 70B. Anther shape: Broadly ovate. Anther length: About 0.5 mm. Anther diameter: About 0.25 mm. Anther color: Close to 70D. Pollen amount: Scarce. Pollen color: Close to 156D. Pistils: Quantity per flower: Two. Pistil length: About 2 mm. Stigma diameter: About 0.1 mm. Stigma shape: Club-shaped. Stigma color: Close to 64A. Style length: About 1 mm. Style color: Close to 64B. Ovary color: Close to 64C.

*Seeds and fruits.*—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25C to 35C and to be suitable for USDA Hardiness Zones 5 through 10.

It is claimed:

1. A new and distinct *Astilbe* plant named 'Go Go Red' as illustrated and described.

* * * * *